United States Patent [19]

MacFarlane et al.

[11] Patent Number: 5,650,288

[45] Date of Patent: Jul. 22, 1997

[54] IMMUNOPHILIN-BOUND IMMUNOSUPPRESSANT ASSAY

[76] Inventors: Gordon D. MacFarlane, 4504 Xerxes Ave. South, Minneapolis, Minn. 55410; Todd L. Jensen, 670 Nebraska, St. Paul, Minn. 55101

[21] Appl. No.: 502,081

[22] Filed: Jul. 14, 1995

[51] Int. Cl.$^6$ .................. G01N 33/53; G01N 33/537; G01N 33/543
[52] U.S. Cl. .................. 435/7.92; 435/7.8; 435/23; 436/501; 436/543
[58] Field of Search .................. 435/7.1, 7.8, 7.92, 435/184, 212, 269, 961, 962, 23; 436/501, 543, 817, 825

[56] References Cited

U.S. PATENT DOCUMENTS

| | | | |
|---|---|---|---|
| 4,727,035 | 2/1988 | Mahoney | 436/518 |
| 4,959,302 | 9/1990 | Cornaby et al. | 435/5 |
| 5,045,452 | 9/1991 | Spragg et al. | 435/7.4 |
| 5,151,348 | 9/1992 | Lau et al. | 435/7.92 |
| 5,169,773 | 12/1992 | Rosenthaler et al. | 435/240.27 |
| 5,202,310 | 4/1993 | Levy et al. | 514/11 |
| 5,279,937 | 1/1994 | Rowe | 435/6 |
| 5,338,684 | 8/1994 | Grenier et al. | 436/8 |
| 5,350,574 | 9/1994 | Erlanger et al. | 514/9 |
| 5,382,655 | 1/1995 | Szánya et al. | 530/317 |
| 5,427,960 | 6/1995 | Wang et al. | 436/536 |
| 5,480,779 | 1/1996 | Fischer et al. | 435/23 |
| 5,489,668 | 2/1996 | Morrison et al. | 530/321 |
| 5,525,523 | 6/1996 | Soldin | 436/503 |

FOREIGN PATENT DOCUMENTS 0293892   12/1993   European Pat. Off. .

OTHER PUBLICATIONS

Chau et al., "A New Extractant for Serum Thyroxine by Enzymatic Digestion of Thyroxine Binding Proteins," J. Clin. Endocrinol Metab. 42(1):189–192 (1976).
Hasler et al., "An $^{125}$I-Labeled Cortisol Radioimmunoassay in which Serum Binding Proteins are Enzymatically Denatured," Clinical Chemistry 22(11):1850–1854 (1976).
Hilgers et al., "Proteolytic Digestion of Genomic Samples Followed by Chelation Inactivation Prior to PCR Amplifications," Bio Techniques 16(1):37, 38 and 40 (1994).
Jones, S.R. et al. Clin. Chem., 31:1910–1911. Nov. 1985.
Donnelly, J.G. et al. Clin. Biochem., 24:71–74. Feb. 1991.
Murthy, J.N. et al. Clin. Chem., 38:1307–1310. Jul. 1992.
Hamberger, C et al. Ther. Drug. Monit., 1988, vol. 10(4), p. 501.
Matouschek, A et al, Proc. Natl Acad. Sci. vol. 92, Jul. 3, 1995, pp 6319–6323.

*Primary Examiner*—James C. Housel
*Assistant Examiner*—Ginny Allen Portner
*Attorney, Agent, or Firm*—Popovich & Wiles, P.A.

[57] ABSTRACT

A method of assaying a sample of blood or blood components for the concentration of an immunophilin ligand comprising incubating the sample with a nonionic detergent and a protease, then inactivating the protease, and subsequently determining the concentration of the immunophilin ligand in the sample.

16 Claims, No Drawings

IMMUNOPHILIN-BOUND IMMUNOSUPPRESSANT ASSAY

TECHNICAL FIELD OF THE INVENTION

The present invention relates to a method of assaying a biological sample for binding of an analyte to an endogenous intracellular receptor or binding protein. In particular, the present invention relates to a method of assaying blood or blood components for binding of an immunosuppressive drug to an immunophilin.

BACKGROUND OF THE INVENTION

The clinical utility of immunosuppressive drugs stems from their ability to prevent graft rejection following organ transplantation. Such drugs exert their effect by inhibiting T-cell activation, which apparently leads to a failure to activate the transcription of early genes that normally function in coordinating the various cells involved in the immune response (Schreiber et at., Immunology Today 13(4): 136–142 (1992)). Those immunosuppressive drugs referred to as immunophilin ligands, which bind specifically to the immunophilin class of endogenous intracellular receptors/binding proteins, differ considerably in structure, yet function similarly, acting as prodrugs, which, upon binding to an immunophilin, form an active complex that exerts a distal effect. For example, cyclosporin A and tacrolimus bind cyclophilin (Handschumacher et al., Science 226: 544–547 (1984); and Harding et al., J. Biol. Chem. 261: 8547–8555 (1986)) and FKBP (Harding et al., Nature 341: 758–760 (1989); Standaert et al., Nature 346: 671–674 (1990); Siekierka et al., Nature 341: 755–757 (1989); and Maki et al., PNAS USA 87: 5440–5443 (1990)), respectively, and the resulting active complex targets the protein phosphatase calcineurin (Liu et al., Cell 66: 807–815 (1991)), the binding of which inhibits T-cell activation. Rapamycin also binds FKBP, although the resulting active complex apparently targets a molecule other than calcineurin (Bierer et al., PNAS USA 87: 9231–9235 (1990)).

A major concern in immunosuppressive therapy associated with organ transplantation is the level of immunosuppressive drug circulating in the blood. Toxicity can result if the immunosuppressive drug level is too high; graft rejection and opportunistic infection can result if the immunosuppressive drug level is too low.

Current methods of assaying for immunosuppressive drugs in the blood involve the use of organic solvents, such as methanol and methylene chloride, to get rid of the immunophilins to which the immunosuppressive drugs bind. Such methods suffer from the disadvantages associated with organic extraction, e.g., performing the extraction procedure under a hood and disposing of the organic waste in accordance with environmental guidelines. In addition, the presence of an organic solvent in high concentration can denature an antibody used to assay the level of the immunophilin ligand in the blood. Although dilution of the organic solvent decreases the likelihood of antibody denaturation, it also dramatically reduces the sensitivity of the assay by so diluting the immunophilin ligand as to impair quantitation of the ligand.

Accordingly, there remains a need for a method of assaying for an immunophilin ligand in blood or blood components that is simpler to perform, i.e., fewer, less complex steps in less time, obviates the need for organic solvents, and provides increased sensitivity and precision over currently available assay methods. Therefore, it is an object of the present invention to provide such a method. Other objects and advantages of the present invention, as well as additional inventive features, will be apparent from the description of the invention provided herein.

SUMMARY OF THE INVENTION

The present invention provides a method of assaying a sample of blood or blood components for the concentration of an immunophilin ligand. The method comprises incubating the sample with a nonionic detergent and a protease to lyse cellular membranes and degrade immunophilins. The protease is then inactivated and the concentration of the immunophilin ligand in the sample is determined. Preferably, the immunophilin ligand is tacrolimus (FK506), cyclosporin (CsA) or rapamycin. The protease is preferably a combination of dispase and thermolysin or a combination of proteinase K and subtilisin. The nonionic detergent is preferably saponin. When the protease is a combination of dispase and thermolysin, the protease is preferably inactivated by addition of a divalent cation chelator in the presence of a zinc salt, whereas, when the protease is a combination of proteinase K and subtilisin, the protease is preferably inactivated by heat. The concentration of immunophilin ligand is preferably determined by an immunoassay or receptor binding assay. Radioimmunoassay (RIA) and enzyme-linked immunosorbant assay (ELISA) are preferred immunoassays. The method of the present invention enables determination of a concentration of an immunophilin ligand as low as around 0.3 ng immunophilin ligand/ml blood or blood components.

DETAILED DESCRIPTION OF THE INVENTION

The present invention overcomes disadvantages inherent to current methods of assaying for the concentration of immunophilin ligands in blood or blood components by providing a simpler method, i.e., fewer, less complex steps to be performed in less time, that obviates the need for organic solvents and provides increased sensitivity and precision over currently available assay methods. Increased sensitivity, in turn, provides the present inventive method with the added advantage of applicability to pediatric, as well as adult, transplant and AIDS patients undergoing immunosuppressive therapy.

Accordingly, the present invention provides a method of assaying a sample of blood or blood components for the concentration of an immunophilin ligand. Given that immunophilins are intracellular, i.e., cytosolic, binding proteins, the sample is preferably whole blood or cellular components thereof, in particular red blood cells or erythrocytes. The method comprises incubating the sample with a nonionic detergent and a protease to lyse any blood cell membranes and degrade immunophilins. The protease is subsequently inactivated and the concentration of the immunophilin ligand in the sample is determined.

The method of the present invention can be used to determine the concentration of any immunophilin ligand, preferably tacrolimus (FK506), cyclosporin, or rapamycin. The method is also generally applicable for all immunophilins, including cyclophilin isoforms, e.g., CyPA, CyPB, CyPC, CyPD, NK-TR, and CyP-40, and FKBP isoforms, e.g., FKBP12, FKBP13, FKBP25, and FKBP52 (Fruman et al., FASEB J. 8: 391–400 (1994)).

The protease used in the method should be one that can degrade the immunophilin, thereby releasing the immunophilin ligand for assay, is resistant to degradation by the nonionic detergent used in the method, and can be inactivated without adversely affecting the sensitivity and the precision of the determination of the concentration of the immunophilin ligand. Care should be taken in obtaining enzymes free from other contaminating enzymes that might not be inactivated by the method of inactivation used. Otherwise, any residual proteolytic activity could degrade an antibody used to determine the concentration of the immunophilin ligand. Preferably, the protease is a combination of proteinase K and subtilisin or a combination of dispase and thermolysin, trypsin, ficin and bromelain may be used.

Proteinase K (Sigma Chemical Co., St. Louis, Mo.) is a nonspecific protease, which cleaves preferentially on the carboxyl side of aliphatic, aromatic and hydrophobic residues. The protease is $Ca^{++}$-dependent but is not inactivated by ethylene diamine tetraacetic acid (EDTA). Rather, it can be inactivated by heat ($\geq 65°$ C.) and by specific protease inhibitors, such as phenyl methyl sulfonyl fluoride (PMSF, Boehringer Mannheim, Indianapolis, Ind.) or diisopropylfluorophosphate (DFP, Calbiochem, La Jolla, Calif.). Heat, e.g., a temperature of $\geq 65°$ C., inactivation is preferred. Subtilisin (Sigma) is also a nonspecific protease, which cleaves preferentially on the carboxyl side of neutral and acidic residues. It is also $Ca^{++}$-dependent and heat-inactivated ($\geq 55°$ C.), although it can be inhibited by acidic pH or a specific protease inhibitor, such as PMSF, DFP or aprotinin. When proteinase K and subtilisin combined are used as the protease, protlolysis is preferably inactivated by heat, e.g., a temperature of $\geq 65°$ C.

Dispase (Boehringer Mannheim or Sigma or Calbiochem) and thermolysin (Sigma or Boehringer Mannheim) are $Ca^{++}$-dependent metallo-proteases and can be inactivated by EDTA, at a concentration of about 5 mM, for example. When dispase and thermolysin combined are used as the protease, proteolysis is preferably inactivated by addition of a divalent cation chelator, such as EDTA, at a concentration of about 5 mM, for example, in the presence of a zinc salt, e.g., $ZnSO_4$, at a concentration of about 40 mM, for example.

Trypsin (Worthingtom Enzymes, Freehold, N.J.) cleaves proteins specifically at the carboxyl side of lysine or arginine residues and can be inhibited by heat ($\geq 90°$ C.) or specifically inhibited by many agents, including aprotinin (Trasylol, Miles, Kankakee, Ill. or Calbiochem), leupeptin (Sigma or Boehringer Mannheim), PMSF, or specific trypsin inhibitors derived from soybean, lima bean or egg white (Worthington or Sigma). Ficin is a thiol protease and can be inactivated by $HgCl_2$, at a concentration of about 2 mM, for example. Bromelain is also a thiol protease and can be inactivated by bromelain inhibitor (Sigma), which is a peptide inhibitor derived from pineapple stem.

The concentration of protease should be high enough degrade to the immunophilins within about 30 min, preferably within about 20 min, yet low enough to allow efficient inactivation of the enzyme but not so low as to compromise the solidity of pellets generated during centrifugation, thereby making pipetting/sample handling more difficult. Accordingly, the concentration of protease should be in the range of about 0.5 to 2.0 units/ml, preferably about 1 unit/ml.

The detergent used in the method should be one that can lyse any cellular membranes present in the sample of blood or blood components, yet it should also be one that does not denature an antibody, if an antibody is used in the determination of the concentration of the immunophilin ligand in the sample. The detergent should also be one whose continued presence in subsequent steps of the assay does not interfere with the assay, itself. Accordingly, ionic detergents, such as sodium dodecyl sulfate (SDS), should be avoided. Preferably, the detergent is saponin. The concentration of nonionic detergent should be high enough to lyse any cellular membranes present in the sample, within about 30 min, preferably within about 20 mins, yet low enough to avoid interference with the determination of the concentration of the immunophilin. Accordingly, the concentration of nonionic detergent should be in the range of about 0.01% to 0.1%, preferably about 0.1%.

The sample of blood or blood components should be incubated with the nonionic detergent and protease under conditions that allow for proteolysis and cell membrane lysis. Preferred conditions include a pH of at least 7, room temperature, and up to about 30 min, preferably up to about 20 min, incubation time.

One of ordinary skill in the art will appreciate that such conditions can be modified and any such modifications can be dictated, in part, by the particular protease and detergent used and their respective concentrations, the specific activity of the protease, whether the sample is whole blood or components thereof, and whether the sample is straight or diluted, for example. Furthermore, one of ordinary skill will appreciate that the sample can be brought in contact with the protease first, the detergent first, or both the protease and detergent at the same time. Preferably, the sample is brought in contact with the detergent first. Most preferably, the sample is brought in contact with both the detergent and the protease simultaneously for convenience and to save time.

The concentration of the immunophilin ligand in the sample can be determined by any one of a number of methods known to those of ordinary skill in the art. Preferably, an immunoassay or receptor binding assay is used. RIA and ELISA are preferred immunoassays. Antibodies, preferably monoclonal antibodies, for use in an immunoassay can be obtained in accordance with methods known to those of skill in the art. Alternatively, monoclonal antibodies specific for tacrolimus and cyclosporin may be obtained from Fujisawa (Osaka, Japan) and Sandoz (Basel, Switzerland), respectively, whereas a monoclonal antibody specific for rapamycin can be obtained from Abbott (Abbott Park, Ill.).

Although theoretically any reasonable sample size can be used, a sample size in the range of 50–150 µl, preferably in the range of 50–125 µl, results in an O-Abs that changes very little and an O-A span that decreases with an increase in sample volume. A 75 µl sample volume maximizes the O-A span and, therefore, should provide increased sensitivity.

The present inventive method enables the determination of an immunophilin concentration of around 0.3 ng/ml of blood or blood components.

The following Examples serve to illustrate the present invention and are not intended to limit its scope.

EXAMPLES

Example 1

This example demonstrates the use of a proteinase K/subtilisin protocol to quantitate tacrolimus levels in whole blood.

A sample of whole blood (75 µl) was placed in a 12×75 mm conical polypropylene tube. A solution of proteinase K (1 U/ml), subtilisin (1 U/ml), Tris, pH=7.2, saponin (0.01%), and $CaCl_2$ (2 mM) was freshly prepared and added (300 µl) to the sample. After mixing thoroughly, the sample was incubated for 20 min at room temperature (RT). Then, the proteases were inactivated by incubation at 70° C. for 15 min. The sample was then vortexed and centrifuged at 2,000×g for 10 min at RT. The supernatant (150 µl) was transferred to microwell plates in duplicate. Monoclonal antibody (mAb, 50 µl) was then added to each well. The supernatant was allowed to incubate with the mAb for 30 min at RT on a shaker set for 700 rpm. Conjugate (50 µl) was then added and incubation was continued for 60 min. The microwell plates were then washed 3× with a plate washer and 3,3',5,5'-tetramethyl-benzidine (TMB; 200 µl) was then added to each well. Incubation was then continued for 15 min at RT on a shaker set for 500 rpm. Stop solution (2N sulfuric acid; 100 µl) was then added to each well and the final solutions were read at 450 nm. The sensitivity of the assay was estimated to be 0.36 ng/ml. Nonspecific binding (NSB)=0.211. Absorbance of the zero standard (O Abs)= 2.655. Difference in absorbance between the zero standard and the A standard (0.3 ng/ml) (O-A Span)=0.132. Difference in absorbance between the A standard and the E standard (30 ng/ml) (A-E Span)=2.186. Difference in absorbance between the E standard and the nonspecific binding (E-NSB Span)=0.126. $ED_{50}$=3.95 ng/ml. Control Values: 1.0 ng/ml (V)=0.97; 3.0 ng/ml (W)=2.58; 5 ng/ml (X)=4.61; 10 ng/ml (Y)=9.08; 25 ng/ml (Z)=23.57.

Example 2

This example demonstrates the use of a thermolysin/dispase protocol to quantitate tacrolimus levels in whole blood.

A sample of whole blood (75 µl) was placed in a 12×75 conical polypropylene tube. A solution of 50 mM Tris, pH 7.2, containing thermolysin (1 U/ml), dispase (1 U/ml), $CaCl_2$ (2 mM), and saponin (0.1%) was freshly prepared and added (300 µl) to the sample. After mixing thoroughly, the sample was incubated for 15 min at RT. Then, the proteases were inactivated by addition of inactivation solution (50 mM Tris, pH 7.2, 40 mM EDTA, 50 mM $ZnSO_4$; 100 µl). The sample (175 µl) was then vortexed, incubated at RT for 30 min, vortexed a second time and transferred to microwell plates in duplicate. mAb (75 µl) was then added to each well. The supernatant was allowed to incubate with the mAb for 60 min at RT on a shaker set for 700 rpm. The microwell plates were then washed 3× with a plate washer. Conjugate (250 µl) was then added to each microwell and incubation was continued for 30 min. The microwell plates were then washed 3× again and TMB (200 µl) was added to each well. Incubation was then continued for 15 min at RT on a shaker set for 500 rpm. Stop solution (100 µl) was then added to each well and the final solutions were read at 450 nm. The sensitivity of the assay was estimated to be 0.2 ng/ml. NSB=0.162. O Abs=2.840. O-A Span=0.263. A-E Span= 2.023. E-NSB Span=0.392. $ED_{50}$=1.31 ng/ml. Control Values: V=0.77. W=2.62. X=4.60. Y=7.23. Z=10.87.

Example 3

This example demonstrates the use of another thermolysin/dispase protocol to quantitate tacrolimus levels in whole blood.

All reagents, standards and controls were used at RT. A sample of whole blood (50 µl) was placed in a 12×75 mm conical polypropylene tube. A thermolysin/dispase solution was prepared as described in Example 2 and allowed to stand at RT for 5 min. The protease solution (300 µl) was then added to the sample. After mixing thoroughly, the sample was incubated for 15 min at RT. The proteases were then inactivated by addition of inactivation solution as described in Example 2. The sample was then vortexed and incubated at RT for 30 min, after which the sample was then vortexed a second time and transferred to microwell plates in duplicate (50 µl). mAb (200 µl) was then added to each well and the sample was allowed to incubate with the mAb for 60 min at RT on a shaker set for 700 rpm. The microwell plates were then washed 3× with a plate washer and conjugate (250 µl) was added to each well. The plates were then incubated for 30 min followed by 3 washes. Chromogen (200 µl) was then added to each well and the plates were allowed to incubate for 15 min before addition of stop solution (100 µl). The plates were then read at 450 nm. NSB=0.162. O Abs=2.840. O-A Span=0.263. A-E Span= 2.023. E-NSB Span=0.392. $ED_{50}$=3.7 ng/ml. Control Values: V=0.73. W=2.72. X=4.31. Y=9.01. Z=21.94. The sensitivity of the assay was estimated to be 0.36 ng/ml. Although this protocol appears to be less sensitive than the protocol of Example 2, it appears to be more reproducible.

Example 4

This example demonstrates the use of the thermolysin/dispase protocol of Example 2 to quantitate cyclosporin levels in whole blood.

A sample of whole blood (50 µl) was placed in a 12×75 mm conical polypropylene tube. A thermolysin/dispase solution was prepared as described in Example 2 and added (300 µl) to the sample. After mixing thoroughly, the sample was incubated for 15 min at RT. Then, the proteases were inactivated as described in Example 2. The concentration of immunophilin ligand present in the sample was then determined using reagents, standards and controls from the INCSTAR CYCLO-Trac SP Whole Blood Kit (INCSTAR, Stillwater, Minn.). $ED_{50}$=244.3 ng/ml.

All of the references cited herein, including patents, patent applications, and publications, are hereby incorporated in their entireties by reference.

While this invention has been described with an emphasis upon a preferred embodiment, it will be obvious to those of ordinary skill in the art that variations in the preferred method can be used, including variations due to improvements in the art. It is intended, therefore, that the invention encompass these variations and that it can be practiced other than as specifically described herein. Accordingly, this invention includes all modifications encompassed within the spirit and scope of the following claims.

What is claimed is:

1. A method of assaying a sample of blood or blood components for the concentration of an immunophilin ligand comprising:
   (a) providing a sample of blood or blood components;
   (b) adding to the sample a nonionic detergent to lyse cellular membranes and two or more proteases to degrade immunophilins;
   (c) incubating the sample;
   (d) inactivating the proteases; and
   (e) determining the concentration of the immunophilin ligand in the sample;
   wherein no organic solvent extraction step is used to remove immunophilins.

2. The method of claim 1 wherein the immunophilin ligand is selected from the group consisting of tacrolimus, cyclosporin, and rapamycin.

3. The method of claim 1 wherein the nonionic detergent is saponin.

4. The method of claim 1 wherein the concentration of the immunophilin ligand in the sample is determined by an immunoassay or receptor binding assay.

5. The method of claim 4 wherein the concentration of the immunophilin ligand in the sample is determined by an immunoassay selected from the group consisting of a radioimmunoassay and an enzyme-linked immunosorbant assay.

6. The method of claim 1 wherein an immunophilin ligand concentration of around 0.3 ng/ml can be detected.

7. A method of assaying a sample of blood or blood components for the concentration of an immunophilin ligand comprising:

(a) providing a sample of blood or blood components;

(b) adding to the sample a nonionic detergent to lyse cellular membranes and two or more proteases to degrade immunophilins, wherein the two or more proteases are selected from the group consisting of dispase and thermolysin combined, and proteinase K and subtilisin combined;

(c) incubating the sample;

(d) inactivating the proteases; and (e) determining the concentration of the immunophilin ligand in the sample;

wherein no organic solvent extraction step is used to remove immunophilins.

8. The method of claim 7 wherein the immunophilin ligand is selected from the group consisting of tacrolimus, cyclosporin, and rapamycin.

9. The method of claim 7 wherein the nonionic detergent is saponin.

10. The method of claim 7 wherein the proteases are dispase and thermolysin combined.

11. The method of claim 7 wherein the proteases are proteinase K and subtilisin combined.

12. The method of claim 10 wherein the proteases are inactivated by addition of a divalent cation chelator and a zinc salt.

13. The method of claim 11 wherein the proteases are inactivated by heat.

14. The method of claim 7 wherein the concentration of the immunophilin ligand in the sample is determined by an immunoassay or receptor binding assay.

15. The method of claim 14 wherein the concentration of the immunophilin ligand in the sample is determined by an immunoassay selected from the group consisting of a radioimmunoassay and an enzyme-linked immunosorbant assay.

16. The method of claim 7 wherein an immunophilin ligand concentration of around 0.3 ng/ml can be detected.

* * * * *